(12) United States Patent
Ohashi

(10) Patent No.: US 9,841,407 B2
(45) Date of Patent: Dec. 12, 2017

(54) LIQUID CHROMATOGRAPH AND LIQUID CHROMATOGRAPH ANALYSIS METHOD

(71) Applicant: SHIMADZU CORPORATION, Kyoto-shi, Kyoto (JP)

(72) Inventor: Hiroshi Ohashi, Otsu (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 46 days.

(21) Appl. No.: 14/636,403

(22) Filed: Mar. 3, 2015

(65) Prior Publication Data

US 2015/0253294 A1 Sep. 10, 2015

(30) Foreign Application Priority Data

Mar. 4, 2014 (JP) .................. 2014-041742

(51) Int. Cl.
   *G01N 30/26* (2006.01)
   *G01N 30/86* (2006.01)
   (Continued)

(52) U.S. Cl.
   CPC .......... *G01N 30/26* (2013.01); *G01N 30/8658* (2013.01); *G01N 30/466* (2013.01); *G01N 30/468* (2013.01); *G01N 2030/342* (2013.01)

(58) Field of Classification Search
   CPC .. G01N 30/26; G01N 30/8658; G01N 30/466; G01N 2030/342; G01N 30/468
   See application file for complete search history.

(56) References Cited

U.S. PATENT DOCUMENTS 4,579,663 A * 4/1986 Poile .................. G01N 30/34
                                                         210/101

2003/0151031 A1 * 8/2003 Li ...................... C08G 61/02
                                                          252/570

FOREIGN PATENT DOCUMENTS

| CN | 102879508 A | 1/2013 |
|----|-------------|--------|
| JP | 2005-227211 A | 8/2005 |
| JP | 2013-24603 A | 2/2013 |

OTHER PUBLICATIONS

Office Action dated Oct. 10, 2016, issued in counterpart Chinese Application No. 201510093224.6, with English tralsation (13 pages).

(Continued)

*Primary Examiner* — Daniel S Larkin
*Assistant Examiner* — Alex Devito
(74) *Attorney, Agent, or Firm* — Westerman, Hattori, Daniels & Adrian, LLP

(57) ABSTRACT

A liquid chromatograph analysis method and a liquid chromatograph minimize analysis time when performing analyses by switching columns and mobile phases. Liquid chromatograph 100 for performing a plurality of analyses according to a schedule table includes: mobile phase switching sections 15, 16 for switching a plurality of mobile phases to select a mobile phase to be used in analysis; column switching sections 31, 33 for switching a plurality of columns 32a-32f to select a column to be used in analysis; and control section 60 including memory 61 for storing an equilibration time of each of the plurality of columns 32a to 32f and an equilibration controller 66 for controlling column equilibration. If used columns or used mobile phases are different between two consecutively executed analyses, equilibration controller 66 equilibrates a column used in the later of the two analyses over an equilibration time read out from memory 61.

4 Claims, 3 Drawing Sheets

(51) Int. Cl.
  *G01N 30/46* (2006.01)
  *G01N 30/34* (2006.01)

(56) References Cited

OTHER PUBLICATIONS

Office Action dated Jun. 6, 2016, issued in counterpart Chinese Patent Application No. 201510093224.6, with English translation. (11 pages).
Office Action dated Oct. 17, 2017, issued in counterpart Japanese Application No. 2014-041742, with English translation (5 pages).
Office Action dated Oct. 5, 2017, issued in counterpart Japanese Application No. 2014-041742, with English translation (6 pages).

* cited by examiner

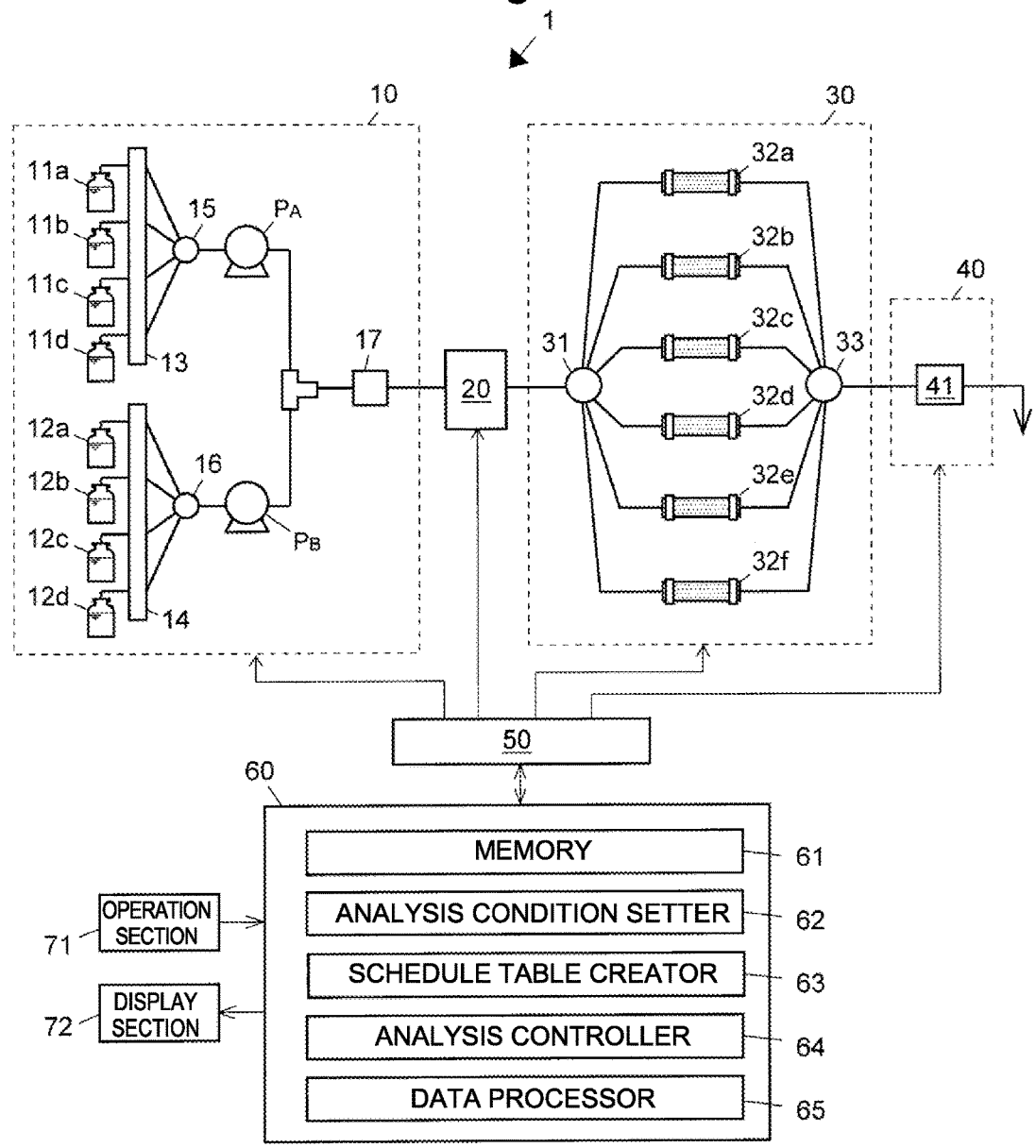

LIQUID CHROMATOGRAPH AND LIQUID CHROMATOGRAPH ANALYSIS METHOD

TECHNICAL FIELD

The present invention relates to a liquid chromatograph, and, more particularly, to a liquid chromatograph in which a plurality of columns and a plurality of mobile phases are switchingly used, and a liquid chromatograph analysis method using the liquid chromatograph.

BACKGROUND ART

A liquid chromatograph is an analysis apparatus in which: a mobile phase (also called eluent) of a liquid and a sample injected into the mobile phase are pressurized by a pump or the like to be caused to pass through a column; and components in the sample are separated and detected based on a difference in interaction (such as adsorption, distribution, ion exchange, and size exclusion) between a stationary phase (also called filler) and the mobile phase in the column.

In the liquid chromatograph, a sample is analyzed under various conditions, in some cases, in order to find the best analysis conditions for the sample (hereinafter, this operation is called method scouting). In the method scouting, the kind of mobile phase, the kind of column, the flow rate of a pump, the temperature of a column oven for heating the column, and the like are set as parameters. Hence, the liquid chromatograph that performs the method scouting is capable of switching these parameters (see Patent Literature 1).

An example of the liquid chromatograph as described above is illustrated in FIG. 4. A liquid chromatograph 1 of FIG. 4 includes: a liquid-sending section 10; an auto-sampler 20; a column oven 30; a detection section 40; a system controller 50 for controlling each of these sections; a control system 60 for managing analysis operations through the system controller 50 and analyzing and processing data obtained by the detection section 40; an operation section 71 including a keyboard and a mouse; and a display section 72 including a display unit. The operation section 71 and the display section 72 are connected to the control system 60. A plurality of columns 32a to 32f are provided in the column oven 30, and the plurality of columns 32a to 32f are switched by passage-switching sections 31 and 33. In the liquid-sending section 10, solvent containers 11a to 11d and solvent containers 12a to 12d are respectively connected to liquid-sending pumps $P_A$ and $P_B$ through deaerators 13 and 14 and solvent-switching valves 15 and 16. Aqueous solvents such as water and aqueous solutions obtained by adding various salts to water are contained in the solvent containers 11a to 11d, and organic solvents such as methanol, acetonitrile, and hexane are contained in the solvent containers 12a to 12d. The aqueous solvents and the organic solvents are mixed with each other by a gradient mixer 17 as needed, whereby a mobile phase having a predetermined composition is prepared.

The mobile phase having the predetermined composition that is prepared by the liquid-sending section 10 passes through the auto-sampler 20 to flow into one of the plurality of columns 32a to 32f in the column oven 30. Before that, a sample is injected into the mobile phase by the auto-sampler 20, and the sample passes through the column while being carried by the flow of the mobile phase. In the process, components in the sample are temporally separated and sequentially detected by the detection section 40 provided with a detector 41 such as a photodiode array (PDA) detector.

Analyses of a number of samples under various analysis conditions are controlled by the control system 60 embodied by a computer, and are automatically processed. The various analysis conditions are described in a file called "method file", which is managed by an analysis condition setter 62 in the control system 60, and is stored in a memory 61 in the control system 60. A schedule table creator 63 in the control system 60 creates a file of data called a "schedule table" which is a table describing which analysis conditions are executed in which order. In the schedule table, a sample to be analyzed and an analysis condition for the sample are described in a row, and a series of rows are listed in the columnar direction as analysis time series. Method files are cited as the analysis conditions. According to the schedule table, an analysis controller 64 in the control system 60 controls each section in the liquid chromatograph 1 such that a series of analyses are executed under the analysis conditions at predetermined timing. A data processor 65 in the control system 60 acquires an analysis result under each analysis condition and performs processes such as chromatogram creation.

CITATION LIST

Patent Literature

[Patent Literature 1] JP 2013-024603 A

SUMMARY OF INVENTION

Technical Problem

Even if the same sample is analyzed, different chromatograms are obtained depending on the kind of mobile phase. Hence, for example, in the case where a sample is analyzed using a different kind of mobile phase from that used in the previous analysis, if the mobile phase used in the previous analysis remains in the column, the succeeding analysis cannot be accurately performed. Hence, in such a case, an operation called "column equilibration" is required until the state where analysis conditions are stable and where the succeeding analysis can be started is attained.

The "column equilibration" is an operation of filling the entire space in the column with a succeeding mobile phase. In this operation, a mobile phase not containing a sample is continuously sent to the column for several minutes to tens of minutes until the amount of mobile phase that is used in the previous analysis and remains in the column becomes negligible.

In the case where a series of analyses, such as method scouting by a liquid chromatograph is performed, the time for the "column equilibration" is placed when the columns and the mobile phases are changed in successive analyses. Conventionally, the time required for the "column equilibration" is set to a fixed value. This simplified setting operations concerning the "column equilibration", and enables a user, instead, to concentrate on setting of a number of analysis conditions.

In the case where the number of columns and the number of mobile phases used in method scouting are small, the number of executions of the column equilibration is also small, and hence the time required for the column equilibrations does not become a particular problem. However, in the case where method scouting is performed using a number of columns and a number of mobile phases, the number of executions of the column equilibration is also large, and hence the time required for the column equilibrations has a large influence on the time required to perform the entire method scouting, leading to an increase in the analysis time.

The present invention, which has been made in view of the above, has an object to provide a liquid chromatograph analysis method and a liquid chromatograph capable of minimizing the analysis time in the case of performing a series of analyses by switching columns and mobile phases.

Solution to Problem

A liquid chromatograph analysis method according to the present invention, which has been made in order to achieve the above-mentioned object, is a liquid chromatograph analysis method in which a sample is analyzed using a liquid chromatograph provided with a function of switching a plurality of columns and a plurality of mobile phases, according to a schedule table in which analysis conditions and execution order of a plurality of analyses are described, the analysis method including the steps of: a) storing an equilibration time of each of the plurality of columns in a memory; b) reading out, from the memory, an equilibration time of a column used in later one of two analyses consecutively executed in the schedule table, in a case where used columns or used mobile phases are different between the two analyses; and c) equilibrating the column used in the later analysis over the equilibration time read out from the memory, immediately before the later analysis is performed.

A liquid chromatograph according to the present invention, which has been made in order to achieve the above-mentioned object, is a liquid chromatograph for analyzing a sample according to a schedule table in which analysis conditions and execution order of a plurality of analyses are described, the liquid chromatograph including: a) a mobile phase switching section for switching a plurality of mobile phases to select a mobile phase to be used in analysis; b) a column switching section for switching a plurality of columns to select a column to be used in analysis; and c) a control section including a memory for storing an equilibration time of each of the plurality of columns and an equilibration controller for controlling column equilibration, wherein, in a case where used columns or used mobile phases are different between two analyses consecutively executed in the schedule table, the equilibration controller reads out, from the memory, an equilibration time of a column used in later one of the two analyses, and equilibrates the column used in the later analysis over the equilibration time read out from the memory, immediately before the later analysis is performed.

In a case where the read-out of the equilibration time of the column used in the later analysis is failed, the equilibration controller may set the equilibration time of the column used in the later analysis to a default value.

Advantageous Effects of Invention

In the liquid chromatograph analysis method and the liquid chromatograph configured as described above according to the present invention, the column equilibration is performed for an equilibration time that is stored in advance for each column. Hence, the column equilibration time can be minimized, and the entire analysis time can be shortened compared with the case where a fixed column equilibration time is used as in a conventional case.

BRIEF DESCRIPTION OF DRAWINGS

FIG. 3 is a diagram illustrating a schedule table created in the present embodiment.

FIG. 4 is a diagram describing a conventional liquid chromatograph.

DESCRIPTION OF EMBODIMENTS

Hereinafter, modes for carrying out the present invention are described by way of embodiments.

Figure 1:
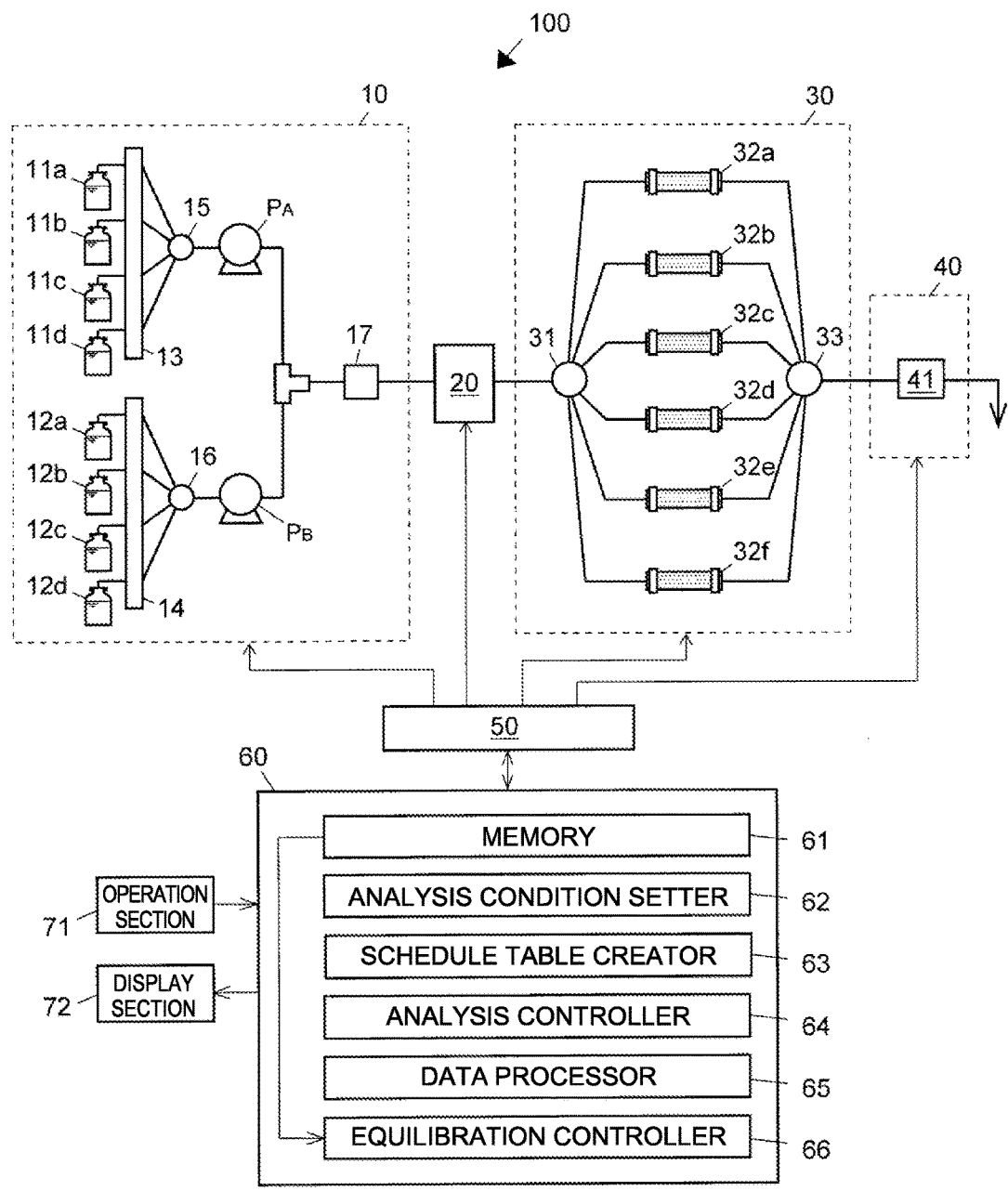
FIG. 1 is a diagram describing a liquid chromatograph according to an embodiment of the present invention.
Figure 2:
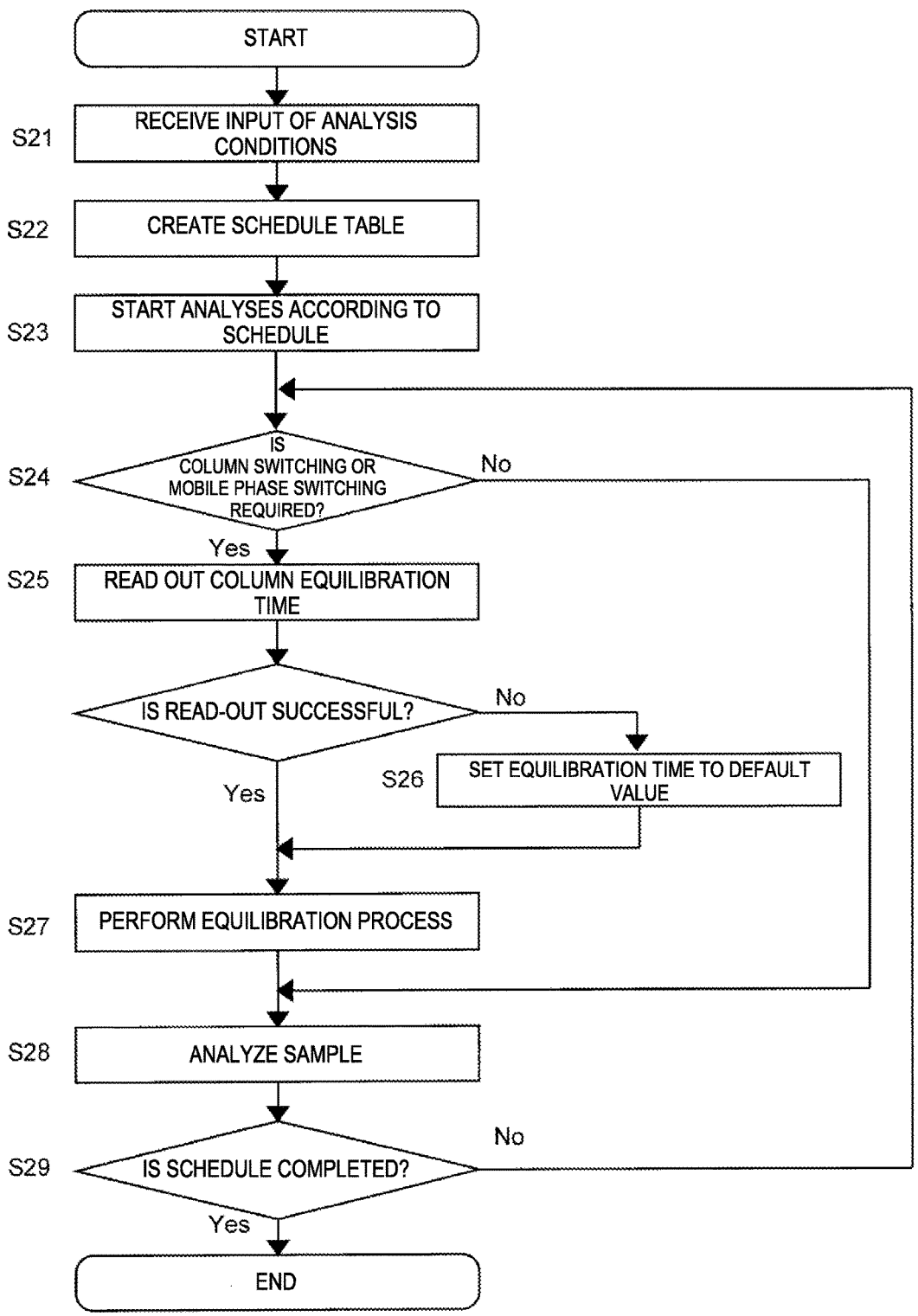
FIG. 2 is a flowchart describing the analysis order of the liquid chromatograph according to the present embodiment.

A liquid chromatograph and an analysis method using the liquid chromatograph of the present embodiment are described with reference to FIG. 1 to FIG. 3. The same constituent elements as those in FIG. 4 are denoted by the same reference signs, and repetitive description thereof is omitted.

A liquid chromatograph 100 of the present embodiment includes a liquid-sending section 10, an auto-sampler 20, a column oven 30, a detection section 40, a system controller 50, a control system 60, an operation section 71, and a display section 72, similarly to the conventional liquid chromatograph 1. The control system 60 includes a memory 61, an analysis condition setter 62, a schedule table creator 63, an analysis controller 64, and a data processor 65, similarly to the conventional liquid chromatograph 1. In addition, the control system 60 includes an equilibration controller 66. Solvent containers 11a to 11d and 12a to 12d and solvent-switching valves 15 and 16 in the liquid-sending section 10 correspond to a mobile phase switching section of the present invention. Moreover, passage-switching sections 31 and 33 correspond to a column switching section of the present invention, and the control system 60 corresponds to a control section of the present invention.

In performing method scouting by the liquid chromatograph 100 of the present embodiment, the equilibration time of each of a plurality of columns 32a to 32f is stored in advance in the memory 61 of the liquid chromatograph 100 of the present embodiment. The equilibration time may be set through calculation based on information such as the capacity of the column, the kind of filler in the column, and the like, and may be empirically set through measurement of a standard sample. The column equilibration time thus stored in the memory 61 is different for each kind of column.

The memory 61 also stores a plurality of method files in which various analysis conditions are described. Operation parameters of the sections of the liquid chromatograph 100 are described in each method file. Examples of the operation parameters include the kind of column and the kind of mobile phase that are used in analysis, the flow rate of a pump, and the temperature of a column oven. The method files are created by the analysis condition setter 62 and stored in the memory 61 in advance based on an instruction that is given by a user through the operation section 71.

In executing method scouting, first, the schedule table creator 63 displays a predetermined setting screen (not illustrated) on the screen of the display section 72, and receives an input by a user through the operation section 71. The user inputs, for each of a plurality of analyses executed in the method scouting, the name of a sample to be analyzed and the injection amount of the sample as well as a method file name used in the analysis and a data file name used to save an analysis result (Step S21).

The schedule table creator 63 creates a schedule table in which the execution order of the plurality of analyses is described, based on the input by the user in Step S21 (Step S22). As a result, for example, such a schedule table as illustrated in FIG. 3 is created.

After the creation of the schedule table, the method scouting is started, and analyses according to designated method files are sequentially executed from the analysis that is described with analysis No. 1 in the schedule table (Step S23).

The equilibration controller 66 checks whether or not column switching or mobile phase switching is required at the time of changing analysis conditions in a series of analyses described in the schedule table (Step S24). Information on a column and a mobile phase used in analysis is not directly described in the schedule table, and is described in a method file cited by the schedule table. Hence, the equilibration controller 66 accesses each method file to check the column and the mobile phase used in analysis.

In the case where the column switching or the mobile phase switching is not required, that is, where the used columns or the used mobile phases are the same between two consecutively executed analyses, for example, in the case where analysis conditions are changed only in the kind of used sample, the column equilibration is not required, and hence processes in Step S25 to Step S27 (to be described later) concerning the equilibration are omitted. The processing immediately goes to Step S28, and the sample is analyzed.

Meanwhile, in the case where the column switching or the mobile phase switching is required, that is, where the used columns or the used mobile phases are different between the two consecutively executed analyses, the equilibration controller 66 reads out the equilibration time of the column used in later one of the two analyses (hereinafter, this column is called "selected column"), from the memory 61 (Step S25). For example, it is assumed in the schedule table illustrated in FIG. 3 that: the column 32a is described as the column used in analysis in "File 1" and "File 2" that are method files respectively cited in analysis Nos. 1 and 2; and the column 32b is described as the column used in analysis in "File 3" that is a method file cited in analysis No. 3. In this case, at the time of switching from the analysis condition of analysis No. 2 to the analysis condition of analysis No. 3, switching of the columns used in analysis (the column 32a→the column 32b) is required. Hence, the equilibration controller 66 reads out the equilibration time of the column 32b from the memory 61. For example, in the case where the equilibration time of the column 32a is stored as 10 minutes and where the equilibration time of the column 32b is stored as 8 minutes, the equilibration controller 66 reads out 8 minutes corresponding to the equilibration time of the selected column, from the memory 61.

In the case where the read-out of the equilibration time of the selected column is failed for the reason that the equilibration time of the selected column is not stored in the memory 61 or other reasons, the equilibration controller 66 sets the equilibration time of the selected column to a default value (Step S26). Examples of the default value include the longest value (for example, 20 minutes) of the column equilibration times usable for the liquid chromatograph 100 of the present embodiment. Because how to deal with a failure in read-out is provided in this way, continuous processing is possible without interruption of various analyses described in the schedule table.

At the timing of switching, the equilibration controller 66 equilibrates the selected column over the equilibration time defined for the selected column (Step S27). In the schedule table illustrated in FIG. 3, at the timing of switching to the analysis of analysis No. 3 after the end of the analysis of analysis No. 2, the equilibration controller 66 equilibrates the column 32b over 8 minutes corresponding to the equilibration time defined for the column 32b. Assuming that a fixed column equilibration time that is conventionally set is 20 minutes, this step can shorten the time required for the series of analyses by 12 minutes.

After the completion of the equilibration of the selected column, sample analysis is started under a new analysis condition using the selected column, under the control of the analysis controller 64 (Step S28).

After the completion of the sample analysis, the analysis controller 64 determines whether or not all the analyses described in the schedule table are completed (Step S29). If all the analyses are not completed, the processing returns to Step S24, and the above-mentioned steps are repeated. If all the analyses are completed, the series of analyses according to the schedule table is ended.

As described above, in the liquid chromatograph 100 of the present embodiment, in the case where the column switching or the mobile phase switching is required in the series of analyses described in the schedule table, the column equilibration is performed over a time that is defined in advance for each kind of column. Hence, the column equilibration time can be minimized, and the entire analysis time can be shortened compared with the case where the fixed column equilibration time is used. Moreover, the mobile phase used during the column equilibration is not wasted. Further, the column use time can be shortened, and hence consumption of the column can be prevented.

Moreover, as the number of analysis conditions described in the schedule table for the method scouting becomes larger, the total time shortened during the column equilibration as described above becomes longer, and hence an increase in time required for the method scouting can be suppressed and the analysis time can be minimized.

In the present embodiment, description is given above of the case where the column switching is required in the series of analyses described in the schedule table, and the same applies to the case where the mobile phase switching is required. For example, in the case where the mobile phase switching (the mobile phase in the solvent container 11a the mobile phase in the solvent container 11b) is required in the series of analyses described in the schedule table illustrated in FIG. 3 while the same column 32a is used, the equilibration controller 66 reads out the equilibration time (10 minutes) of the column 32a from the memory 61, and equilibrates the column 32a over the read-out equilibration time. Also in this case, assuming that the fixed column equilibration time that is conventionally set is 20 minutes, this step can shorten the time required for the series of analyses by 10 minutes.

Moreover, in the present embodiment, description is given above of the example where, after the start of the analyses according to the schedule table, whether or not the column switching or the mobile phase switching is required is checked each time analysis conditions are changed, but timing to check the column switching or the mobile phase switching is not limited thereto. For example, at the time of creating the schedule table, the method files used in all the analyses described in the schedule table may be checked, and whether or not the column switching or the mobile phase switching is required may be checked before each analysis. In this case, at the time of creating the schedule table, if the user designates a method file for using a column whose equilibration time is not stored in the memory 61, a warning to that effect may be given to the user.

REFERENCE SIGNS LIST

1, 100 . . . Liquid Chromatograph
10 . . . Liquid-Sending Section
11a to 11d, 12a to 12d . . . Solvent Container
13, 14 . . . Deaerator
15, 16 . . . Solvent-Switching Valve
17 . . . Gradient Mixer
20 . . . Auto-Sampler
30 . . . Column Oven
31, 33 . . . Passage-Switching Section
32a to 32f . . . Column
40 . . . Detection Section
41 . . . Detector
50 . . . System Controller
60 . . . Control System
61 . . . Memory
62 . . . Analysis Condition Setter
63 . . . Schedule Table Creator
64 . . . Analysis Controller
65 . . . Data Processor
66 . . . Equilibration Controller
71 . . . Operation Section
72 . . . Display Section

The invention claimed is:

1. A liquid chromatograph analysis method in which a sample is analyzed using a liquid chromatograph provided with a function of switching a plurality of columns and a plurality of mobile phases, according to a schedule table in which analysis conditions and execution order of a plurality of analyses are described, the analysis method comprising the steps of:
  a) storing an equilibration time of each of the plurality of columns in a memory;
  b) reading out, from the memory, an equilibration time of a column used in later one of two analyses consecutively executed in the schedule table, in a case where used columns or used mobile phases are different between the two analyses; and
  c) equilibrating the column used in the later analysis over the equilibration time read out from the memory, immediately before the later analysis is performed.

2. The liquid chromatograph analysis method according to claim 1, further comprising setting the equilibration time of the column used in the later analysis to a default value, in a case where the read-out of the equilibration time of the column used in the later analysis is failed.

3. A liquid chromatograph for analyzing a sample according to a schedule table in which analysis conditions and execution order of a plurality of analyses are described, the liquid chromatograph comprising:
  a) a mobile phase switching section for switching a plurality of mobile phases to select a mobile phase to be used in analysis;
  b) a column switching section for switching a plurality of columns to select a column to be used in analysis; and
  c) a control section including a memory for storing an equilibration time of each of the plurality of columns and an equilibration controller for controlling column equilibration, wherein
  in a case where used columns or used mobile phases are different between two analyses consecutively executed in the schedule table, the equilibration controller reads out, from the memory, an equilibration time of a column used in later one of the two analyses, and equilibrates the column used in the later analysis over the equilibration time read out from the memory, immediately before the later analysis is performed.

4. The liquid chromatograph according to claim 3, wherein, in a case where the read-out of the equilibration time of the column used in the later analysis is failed, the equilibration time of the column used in the later analysis is set to a default value.

* * * * *